United States Patent [19]
Kofod

[11] Patent Number: 4,854,870
[45] Date of Patent: Aug. 8, 1989

[54] CLEANING TOOL, ESPECIALLY FOR DENTAL USE

[76] Inventor: Finn Kofod, Pilegardsvej 3, Rønne, Denmark, 3700

[21] Appl. No.: 35,999

[22] PCT Filed: Jul. 7, 1986

[86] PCT No.: PCT/DK86/00079
§ 371 Date: Mar. 10, 1987
§ 102(e) Date: Mar. 10, 1987

[87] PCT Pub. No.: WO87/00032
PCT Pub. Date: Jan. 15, 1987

[30] Foreign Application Priority Data
Jul. 11, 1985 [DK] Denmark .............................. 3163/85

[51] Int. Cl.⁴ ................................................ A61C 3/06
[52] U.S. Cl. ..................................... 433/166; 433/142
[58] Field of Search ......................... 433/125, 142, 166

[56] References Cited
U.S. PATENT DOCUMENTS

| | | | |
|---|---|---|---|
| 441,524 | 11/1890 | Whitcomb | 433/166 |
| 781,587 | 1/1905 | Blake | 433/166 |
| 1,497,759 | 6/1924 | Lowe | 433/166 |
| 2,017,881 | 10/1935 | Wiseman | 433/166 |
| 2,093,006 | 9/1937 | Chott | 433/166 |
| 3,599,333 | 8/1971 | Muhler | 433/166 |
| 3,621,577 | 11/1971 | Spinello | 433/166 |
| 4,259,071 | 3/1981 | Warden et al. | 433/166 |

Primary Examiner—Gene Mancene
Assistant Examiner—Adriene J. Lepiane
Attorney, Agent, or Firm—Darby & Darby

[57] ABSTRACT

A dental cleaning tool comprises a rotatable cleaning body of an elastically yielding material formed in a cuplike concavity extending inward from a rim and where curved ribs having triangular cross-section extend from the rim towards the center of the cup to a point removed from the center so as to provide a free zone at the center of the cup.

9 Claims, 1 Drawing Sheet

CLEANING TOOL, ESPECIALLY FOR DENTAL USE

BACKGROUND OF THE INVENTION

The invention relates to a cleaning tool, especially for dental use, with a rotary shaft, at the free end of which a detachable cleaning body of an elastically yielding material can be mounted, said body at the end being hollowed to form a cup-like concavity extending inwardes from the rim, and where ribs extend inwards from the rim in the cup.

Tools of this sort are applied for dental use for cleaning and polishing tooth faces, where the scraping and polishing body when used by dentists is secured to the driving shaft in the angle piece. In use a paste-like or liquid abrasive, polishing agent or disinfectant is applied, which by means of the rotary body is brought to act on the tooth face.

Moreover, such a body can be mounted on other types of rotary shafts, such as electric toothbrushes with rotary brushes, where the user can operate the tool himself.

In this way the tooth faces can be cleaned effectively for plaque and other impurities.

However, this cleaning and the usual daily brushing of teeth and gum has no prophylactic effect on the serious tooth disease, paradentosis. With this disease teeth may loosen because the jawbone and the surrounding tissue are slowly decomposed. The disease gives hardly any sypmtoms and will therefore often be at a very advanced state before it is detected.

The disease is caused by enzymes and other bacteriological products given off by such bacteria as are always present in any mouth. Paradentosis develops in the small open gingival pockets around the teeth, where it is not possible to remove those coatings on the teeth, on which the bacteria thrive. If the bacteria are left to accumulate, inflammation of the surrounding gum will occur. The inflammation will spread, and the enzymes will attack the fibres of the periodontal connecting the bone with the tooth. When these fibres are decomposed, the bone will retract itself, and the tooth will be left with still less to be rooted in, so that eventually it becomes loose and may fall out.

Paradentosis is treated by removing the bacteria accumulations and making sure they do not reform.

If the accumulations are deep down in a gingival pocket, it can be difficult to get access to it, and surgery will often be necessary to remove inflamed gum in order to get access to the pocket and stop the attack.

The problem is that even daily careful toothbrushing offers no protection against paradentosis since as previously mentioned, it is practically impossible to clean the gingival pockets properly.

SUMMARY OF THE INVENTION

It is the object of the invention to provide a cleaning tool that overcomes these drawbacks, and which makes the cleaning of particularly the gingival pockets possible, and which at the same time is so simple to use that most people can apply the tool themselves, and this is achieved by a cleaning body, the ribs of which describe a curve from the rim of the body toward its centre and in such a manner that tht point of the ribs being furthest toward the rim is frontmost in the direction of rotation of the body, and with the top of the curve pointing backwards in the direction of rotation.

By designing the body with such a rib shape, it will in use be able to remove coatings in the gingival pocket in that the ribs wil take the removed coatings toward the centre of the cup. This travelling is due to the ribs being designed like pump wheels, which means that an even flow of cleaning agent will take place from the outer of the body and inwards and the removed leavings will be led inwards simultaneously.

By this method an optimum removal of coatings from the tooth face is achieved, and because the body is comparatively thin near the rim, this can be moved deep down into the gingival pocket and clean this whereby an optimum cleaning and consequently an effective prevention of paradentosis attack is achieved. Finally, an expedient massaging of the gum in the rim zone is achieved, whereby the gum is strengthened and tightened in order to reduce the size of the gingival pockets.

By, as related to in claim 2, providing the ribs with a sharp edge facing the tooth face, the highest degree possible of elasticity and thereby the ability for the rib to adapt themselves to the tooth profile is achieved.

By, as related to in claim 3, designing the ribs with a downward slope in the direction of rotation, an effective scraping effect is achieved.

Finally, it is expedient, as related to in claim 4, to design the ribs in such a manner that they stop a distance from the centre leaving a hollow space where the removed coating material and the cleaning agent will be accumulated.

BRIEF DESCRIPTION OF THE DRAWING

In the following the invention shall be described with reference to the drawing, wherein.

DESCRIPTION OF THE PREFERRED EMBODIMENT

Figure 1:
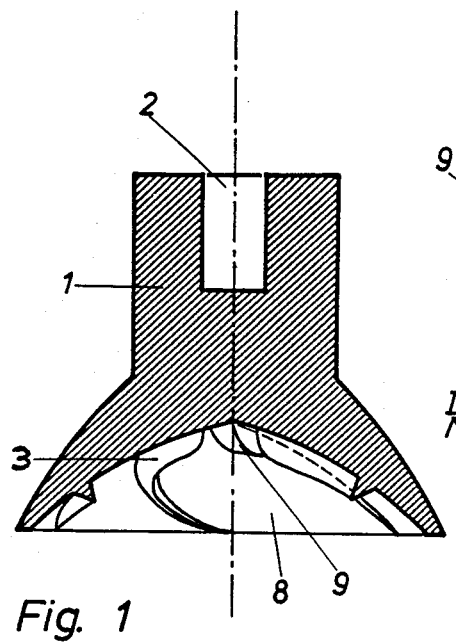
FIG. 1 shows a section through a cleaning body, seen along I—I in FIG. 2.

In the drawing is shown an example of a preferred embodiment of a cleaning body according to the invention.

Figure 2:
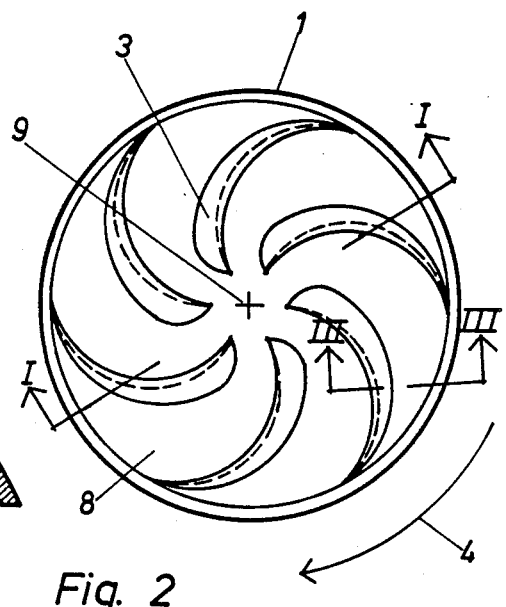
FIG. 2 shows a bottom view of the body.

FIGS. 1 and 2 show the actual body 1, which is primarily made by casting of rubber or plastics with elastic and yielding qualities.

The dimension of the body depends on the purpose it is to serve, but for dental use a diameter of 10 mm for the actual operating part will be suitable. With smaller teeth a correspondingly smaller body is preferred.

The body 1 cõmprises an upper holding or coupling part with a blind hole 2 for the shaft, which is not shown, for rotating the body in the direction of rotation 4 indicated by an arrow.

Below this part the body widens to form the operating part. This consists of a cup-like hollowing 8, which extends from the rim zone of the body to the centre 9 of the body, which centre is usually identical with the axis of rotation.

In the inside of the cup 8 protruding ribs 3 are provided, as shown in a bottom view in FIG. 2, which ribs describe a curve whose highest point lies rearmost in the direction of rotation 4 of the body.

Moreover, it is seen from the drawing that the part of the ribs 3 lying furthest out points forwards in the direction of rotation 4.

Figure 3:
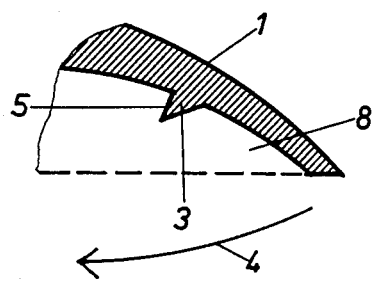
FIG. 3 shows a partial section through a rib, seen along III—III in FIG. 2.

In FIG. 3 is shown a cross section of a rib. It is seen that the rib has a triangular cross section in that it is pointed toward the centre of the cup 8. Moreover, it is asymmetrical in that the front face 5 of the rib in the direction of rotation 4 makes an acute angle with the side wall of the cup 8. Hereby is produced an effective scraping edge which can remove the coatings on the tooth face.

The number of ribs 3 may vary according to requirements, but there should be a suitable distance between them, because there must be a passage for the cleaning agent and any fluid flowing through.

It is furthermore seen that the ribs 3 stop a distance from the centre 9, whereby a hollow space is obtained in which the cleaned out material can accumulate when the material is removed and carried inwards. By suitable cleaning of the body and rinsing of the mouth the removed material can be led away.

Figure 4:
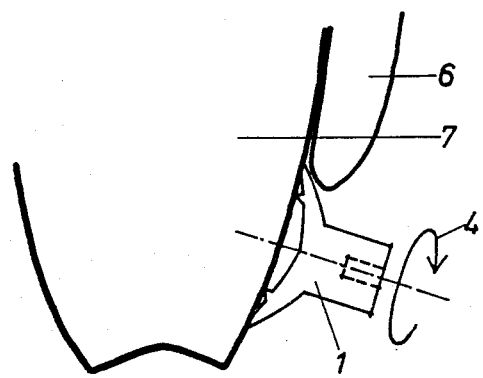
FIG. 4 shows a side view of the cleaning body in use.

Finally, it is seen in FIG. 4, how the body 1 is applied for cleaning a gingival pocket formed between a tooth 7 and the surrounding gum 6. During turning of the body 1 the ribs 3 scrape the tooth face right down to the bottom of the gingival pocket.

By suitable dimensioning of the operating part of the body 1, the rim zone can be made thinner or thicker and the diameter larger or smaller in order that even the deepest pockets can be cleaned, and thereby always obtain the best possible removal of pathogenic coatings.

I claim:

1. A dental cleaning body adpated for removable mounting at an end of a rotary shaft, comprising
    said cleaning body made of an elastically yielding material having a first end provided with a bore for receiving the end of the shaft, a second having a cavity extending from an outer edge thereof in the direction of said first end, curved ribs extending in the cavity from said outer edge inwardly, each said rib having a substantially triangular cross section with a front side turning forwardly in the direction of rotation and a rear side forming a sharp edge on each said rib, said cavity having a concaved configuration so that the entire sharp edge of each said rib rests on a surface of a tooth during the rotation of the cleaning body, a curvature of each said rib differs only slightly from a straight line, an outermost point of each said rib located at the outer edge lies frontmost in the direction of rotation and its radially innermost point rearmost in the direction of rotation.

2. A dental cleaning body according to claim 1 wherein the cavity has a center and the width of each said rib decreases from a position at said outer edge toward the center of the cavity.

3. A dental cleaning body according to claim 2, characterized in that the front side of each said rib in the direction of rotation forms an angle with the rear side, said angle being 90° or less.

4. A dental cleaning body according to claim 2, characterized in that each said rib extends from the outer edge of the body to a place a distance removed from the center of the cavity.

5. A dental cleaning body according to claim 1 wherein the cavity has a center and the front side of each said rib in the direction of rotation forms an angle with the rear side, said angle being 90° or less.

6. A dental cleaning body according to claim 5, characterized in that each said rib extends from the outer edge of the body to a place a distance removed from the center of the cavity.

7. A dental cleaning body according to claim 1 wherein the cavity has a center and each said rib extends from the outer edge of the body to a place a distance removed from the center of the cavity.

8. A dental cleaning body according to claim 1, wherein an angular difference between the radially outermost and innermost point of the ribs is only small.

9. An elastic dental cleaning body adapted for removable mounting at a free end of a rotary shaft comprising
    said body having a first end adpated to receive said rotary shaft and a secnd end having an outer edge,
    said body having an inner cavity extending from the outer edge in the direction of said first end, said inner cavity having a concaved configuration with a center thereof located near said first end,
    a plurality of ribs symmetrically disposed within the inner cavity,
    said ribs having slightly curved configuration extending from said outer edge along an inner wall of the concaved inner cavity in the direction of the center thereof in such a manner that a substantial, empty area free of any ribs and obstructions is defined near the center of the inner cavity,
    each said rib having front and rear surfaces, said front surface facing the direction of rotation of the body is exposed at an acute angle to the inner wall of the cavity in such a manner that said front surface crosses the rear surface defining a scraping edge of the rib, said scraping edge facing the direction of the rotation of the body, and extends along the entire length of the rib,
    whereby during operation of said body said front surface of the rib engages a tooth enabling said scraping edge to remove a coating from a surface thereof.

* * * * *